United States Patent [19]

Sasaki

[11] Patent Number: 5,065,766
[45] Date of Patent: Nov. 19, 1991

[54] DEVICE FOR DETECTING R-WAVES IN ELECTROCARDIOGRAM

[75] Inventor: Minoru Sasaki, Yokohama, Japan

[73] Assignee: Kabushiki Kaisya Advance Kaihatsu Kenkyujo, Japan

[21] Appl. No.: 336,540

[22] PCT Filed: Aug. 12, 1985

[86] PCT No.: PCT/JP85/00448
§ 371 Date: Apr. 10, 1986
§ 102(e) Date: Apr. 10, 1986

[87] PCT Pub. No.: WO86/01092
PCT Pub. Date: Feb. 27, 1986

Related U.S. Application Data

[62] Division of Ser. No. 855,611, Apr. 10, 1986, abandoned.

[30] Foreign Application Priority Data

Aug. 11, 1984 [JP] Japan ................................ 59-167296

[51] Int. Cl.5 .......................................... A61B 5/0402
[52] U.S. Cl. .................................................. 128/708
[58] Field of Search ...................... 128/696, 702-704, 128/708

[56] References Cited

U.S. PATENT DOCUMENTS 3,590,811 7/1971 Harris .................................. 128/708
3,939,824 2/1976 Arneson et al. .................... 128/708
4,216,780 8/1980 Rubel et al. .
4,240,442 12/1980 Andresen et al. ................... 128/708

FOREIGN PATENT DOCUMENTS 49-24426 6/1974 Japan .
50-82881 7/1975 Japan .
50-90188 7/1975 Japan .
5613926 7/1975 Japan .

OTHER PUBLICATIONS

Dimmick et al., IBM Technical Disclosure Bulletin, "Physiological Monitor System", vol. 19, No. 3, Aug. 1976, pp. 776-778.

Primary Examiner—Ruth S. Smith
Attorney, Agent, or Firm—Finnegan, Henderson, Farabow, Garrett & Dunner

[57] ABSTRACT

A device for detecting an R-wave in an electrocardiogram, comprising a filter for passing a frequency band including the R-wave and a peak hold circuit for forming R-wave pulse signals from signals passed through the filter by holding the peak phase of the R-wave. According to the device for detecting an R-wave in an electrocardiogram, the R-wave in an electrocardiogram can be effectively discriminated from noise, and also an R-wave deformed by arrhythmia can be stably detected.

2 Claims, 5 Drawing Sheets

# DEVICE FOR DETECTING R-WAVES IN ELECTROCARDIOGRAM

This application is a division of application Ser. No. 855,611, filed Apr. 10, 1986, now abandoned.

TECHNICAL FIELD

The present invention relates to a device for detecting R-waves in an electrocardiogram, which device can positively detect R-waves from among electrocardiographic wave patterns

BACKGROUND ART

Various means have hitherto been employed for the positive detection of R-waves in an electrocardiogram. The method most generally used comprises passing the frequency band including the R-waves though a filter and generating pulses by a single stable multi-vibrator when a predetermined threshold value is surpassed. Such a method may be effective for performing a simple count of a heart rate, but it is not suitable for reading information including various bits of phase information from electrocardiographic wave patterns, since it cannot recognize the peak phase (time phase) of an R-wave. Further, if arrhythmia or a normal R-wave appears together with the artifact through lung or body movement, a problem arises in that it is difficult to accurately detect and recognize the arrhythmia or normal R-wave due to a change in the wave pattern.

DISCLOSURE OF THE INVENTION

An object of the present invention is to solve the problems of the prior art mentioned above by providing a device for detecting R-waves in an electrocardiogram, in which R-wave pulses are generated by holding the phase (time phase) of the R-wave, more preferably by correspondingly changing the reference voltage in order to discriminate the R-wave from a T-wave or noise.

The device of the present invention for detecting an R-wave in an electrocardiogram comprises a filter for passing a frequency band including the R-wave in an electrocardiogram and a peak hold circuit for forming R-wave pulse signals from the signals passed through the above filter by holding the peak phase of the R-wave and the voltage.

PREFERRED EMBODIMENTS FOR CARRYING OUT THE INVENTION

Preferable embodiments of the present invention will be now explained with reference to the drawings.

Figure 1:
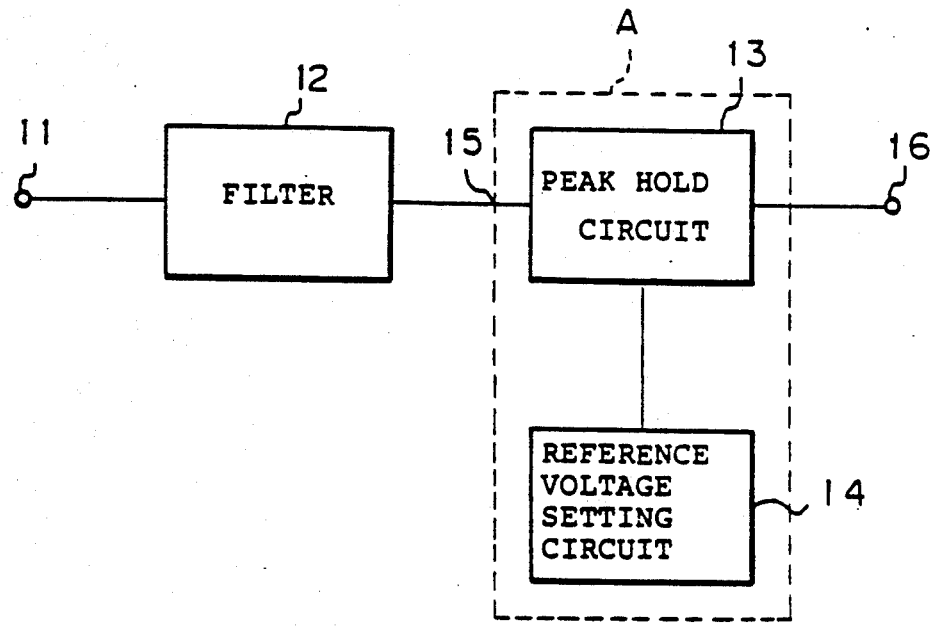
FIG. 1 is a block diagram of the R-wave detecting device of the present invention.

FIG. 1 is a block diagram of the device for detecting R-waves in an electrocardiogram, according to the present invention. The block diagram shows an electrocardiogram input terminal (11), a filter (12) for passing frequency components including an R-wave from the electrocardiogram input, a peak hold circuit (13) for forming R-wave pulses, a reference voltage setting means (14) for setting the reference voltage value of the above peak hold circuit (13), and an output terminal (16) for outputting R-wave pulses.

Figure 2:
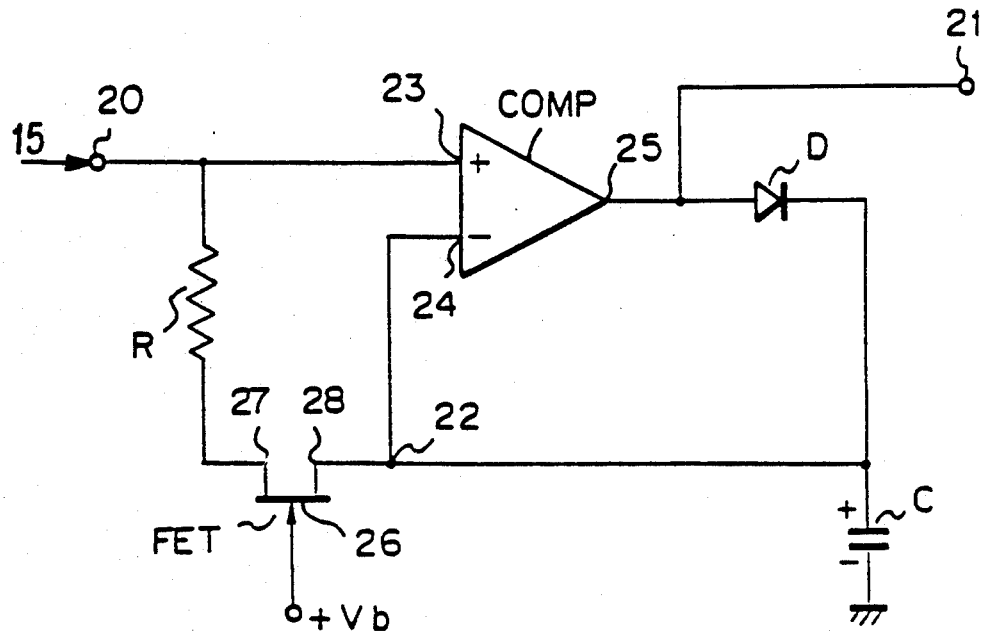
FIG. 2 is a circuit diagram of the portion A enclosed within the broken line in FIG. 1.

The peak hold circuit (13) enclosed within the broken line in FIG. 1 consists of a comparator (COMP), a diode (D), a capacitor (C), and a resistance (R), as shown in FIG. 2. The reference voltage setting circuit (14) of the portion A enclosed within the broken line in FIG. 1 consists of a field effect transistor (FET) and a bias voltage +Vb.

The input terminal (20) for supplying an R-wave is connected to the non-reversal input terminal (23) of the comparator (COMP), the output (25) of the comparator (COMP) is supplied to the pulse output (21), and is also connected through the diode (D) to the (+) terminal of the capacitor (C). The output of the (+) terminal of (24) of the comparator (COMP), and is also connected to the terminal (28) of the field effect transistor (FET). A bias voltage +Vb is supplied to the terminal (26) of the field effect transistor (FET). Here, the voltage $E_2$ at the reversal input terminal (24) of the comparator (COMP) shown in FIG. 3(c) can be set higher than the amplitude value of the T-wave in the time phase of a T-wave, and $E_3$ can be set at a constant voltage higher than the noise in the electrocardiogram, for example, at a value relative to the R-wave, amplitude voltage $E_1$, i.e., at approximately $E_3 = \frac{1}{2}(E_1)$ (V) (hereinafter $E_2$ is referred to as the first reference voltage, and $E_3$ as the second reference voltage).

Figure 3:
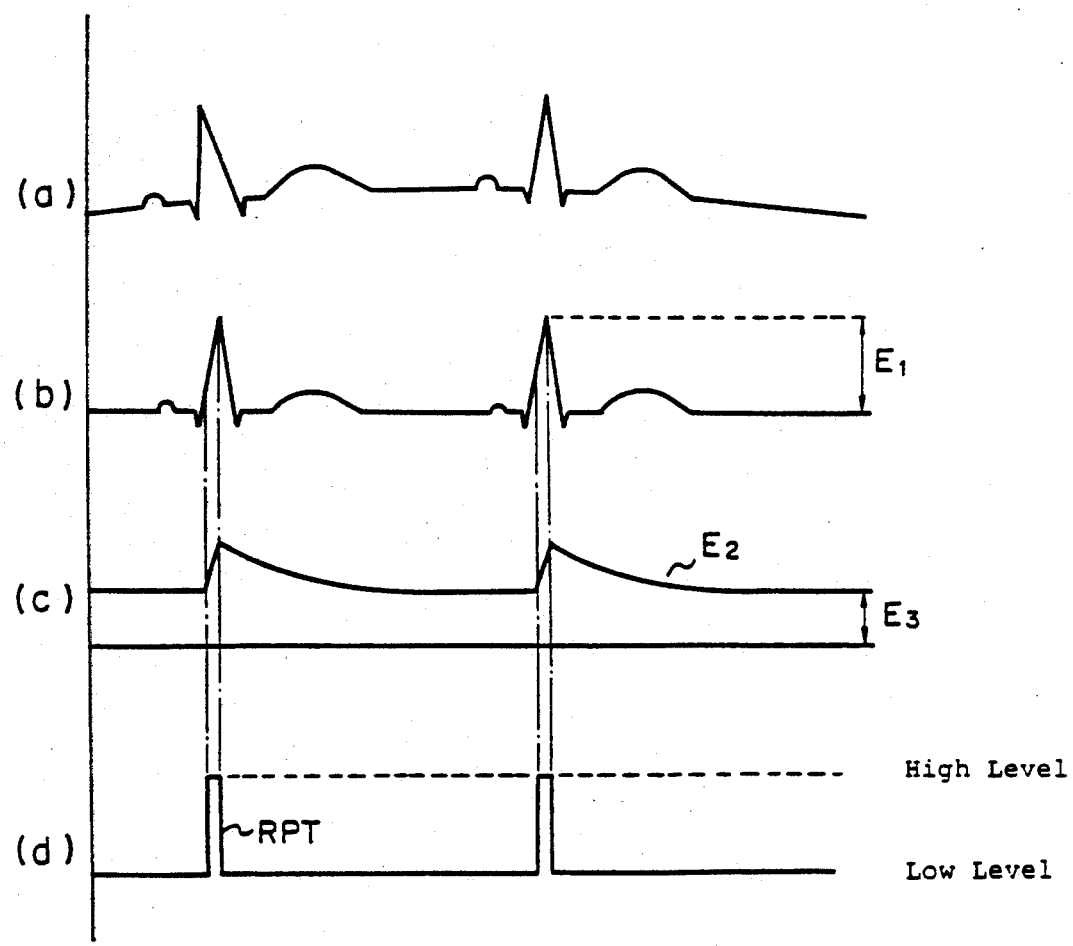
FIG. 3 shows the wave patterns of the respective portions in FIG. 1 and FIG. 2.

Referring next to the wave patterns at the respective portions as shown in FIG. 3, the operation of the device for detecting an R-wave in an electrocardiogram constituted as described above is explained.

An electrocardiographic wave pattern shown in FIG. 3(a) is input to the input terminal (11) shown in FIG. 1. The wave pattern is converted by the filter (12) to a wave pattern as shown in FIG. 3(b). The signal, (15) thus converted is input to the input terminal (28) in FIG. 2. The second reference voltage $E_3$ (V) is supplied to the reversal input terminal (24) of the comparator (COMP). The second reference voltage $E_3$ is determined by the capacitor (C) and the field effect transistor (FET). The voltage in FIG. 2 (22) is shown in FIG. 3. When the wave pattern of FIG. 3(b) input to the non-reversal input terminal (23) of the comparator (COMP) surpasses the second reference voltage $E_3$, the output (25) of the comparator (COMP) becomes high level, as shown in FIG. 3(d). Under this condition, the output (25) of the comparator (COMP) charges the capacitor (C) through the diode (D) as shown in FIG. 3(c). Consequently, the potentials of the terminal (28) of the field effect transistor (FET) and the reversal input terminal (24) of the comparator (COMP) are elevated.

Next, when the peak of the R-wave signal input to the input terminal (20) has passed, the potential of the non-reversal input terminal (23) and the reversal input terminal (24) of the comparator become reversed by the voltage of the charged capacitor (C), whereby the output (25) of the comparator (COMP) becomes low level, as shown in FIG. 3(d), exhibiting the peak phase (time phase) of R-wave RPT (the peak phase or time phase of the R-wave, as shown in FIG. 3). When the output (25) of the comparator (COMP) becomes low level, the charged capacitor (C) initiates a discharge through the field effect transistor (FET), whereby the first reference voltage ($E_2$) drops as shown in FIG. 3(c). As the terminal (28) of the field effect transistor (FET) approaches the bias voltage +Vb of the terminal (26) of the field effect transistor voltage (FET) previously set, the discharge voltage is reduced until discharge is stopped on reaching the second reference voltage ($E_3$) shown in FIG. 3(c), and the field effect transistor (FET) holds the second reference voltage ($E_3$). Thus, since the peak amplitude voltage of the R-wave constantly arrived at is made the peak value of the first reference voltage ($E_2$), and the second reference voltage is held before the next R-wave arrives, the first reference voltage is determined by the R-wave peak amplitude value of the previous amplitude.

Next, another example according to the present invention is described.

Figure 4:
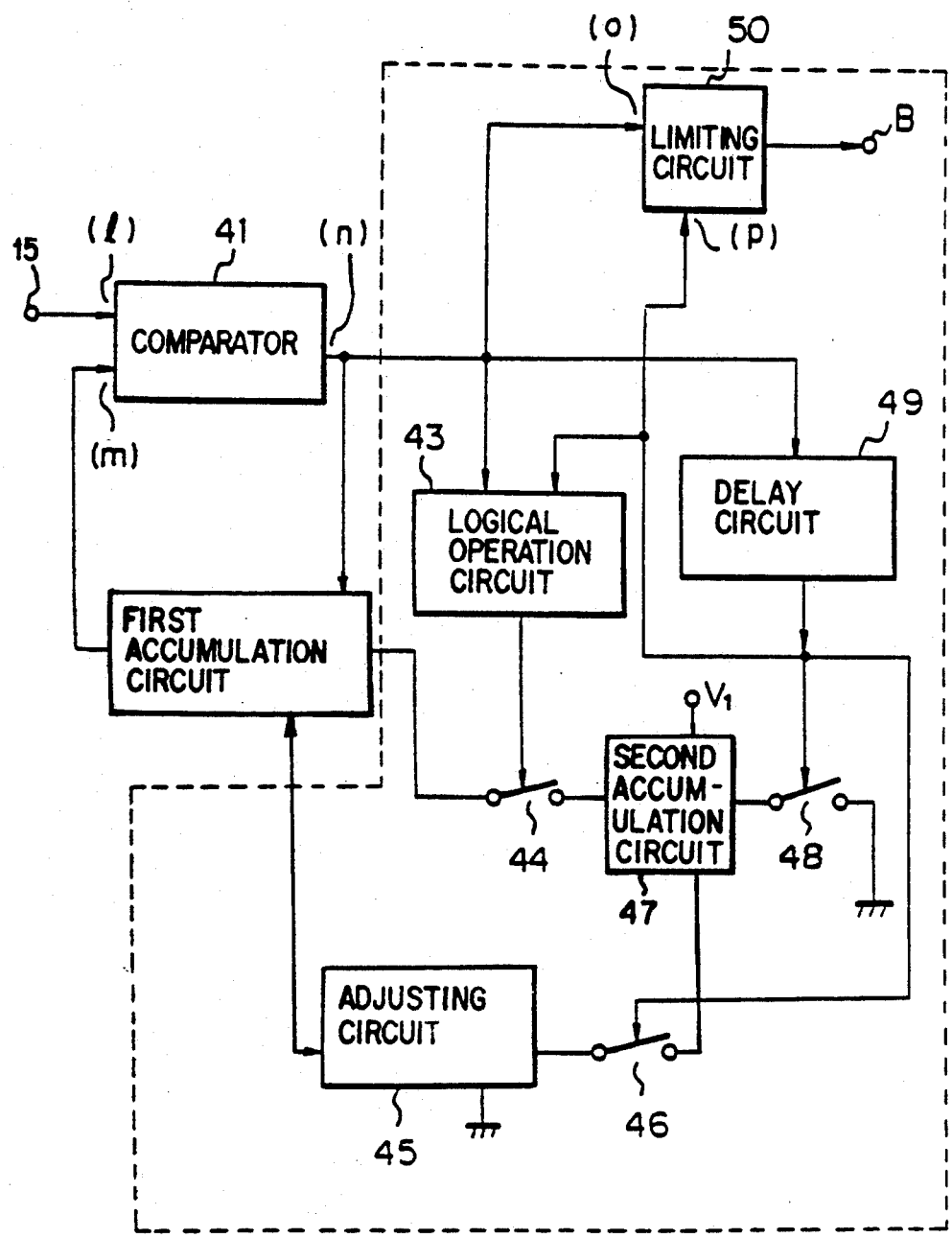
FIG. 4 is a block diagram showing another example of the portion A enclosed within the broken line in FIG. 1.

FIG. 4 is a block diagram showing another example of the device for detecting an R-wave in an electrocardiogram according to the present invention. In the Figure, the portion enclosed within the broken line corresponds to the reference voltage setting circuit (14) of the embodiment shown in FIG. 1. In FIG. 4, the reference numeral (42) is the first accumulation circuit. The first accumulation circuit (42) is a means for accumulating charges and corresponds to the capacitor (C) in the embodiment in FIG. 2. The reference numeral (43) is a logical operation circuit The logical operation circuit (43) has two inputs, and when both the inputs are at the "0" level, the output becomes "1" level. The reference numeral (45) is an adjusting circuit This adjusting circuit (45) is provided for erasing a voltage greater than the standard input, by determining that input as the standard input and comparing the voltages of other inputs with that of the standard input, and a known circuit such as a clamping circuit may be used. The reference numeral (47) is the second accumulation circuit. The second accumulation circuit (47) is constantly supplied with a voltage of $V_1$ (V), and is provided to accumulate charges as for the above first accumulation circuit. Such an accumulation circuit can be constructed of, for example, a parallel circuit of a resistance and a capacitor. The reference numeral (49) is a delay circuit. The delay circuit is provided for delaying the digital pulse in time. The reference numeral (50) is a limiting circuit. The limiting circuit (50) is arranged on the output side of the comparator (41) for outputting R-wave pulses through the limiting circuit (50) and operates as a circuit for outputting a compulsory "0" level output at the time zone with the pulse width of the delayed output pulse which is the output from the delay circuit (49), and can be constructed of, for example, a combination with a switching circuit or a logical operation circuit. In other words, the limiting circuit (50) is provided for a more correct detection of an R-wave in the case when the T-wave has a higher amplitude than the R-wave, and is another advantageous embodiment of the reference voltage setting means of the present invention. In FIG. 4, the reference numerals (44), (46) and (48) are switches, respectively, and each is provided so as to be closed when the respective outputs of the logical operation circuit (43) and the delay circuit (49) become "1".

The voltage $V_1$ (V) exhibited by the second accumulation circuit (47) set as described above exhibits the same voltage value as the second reference voltage $E_3$ in the first example of the device for detecting an R-wave in an electrocardiogram according to the present invention.

Figure 5:
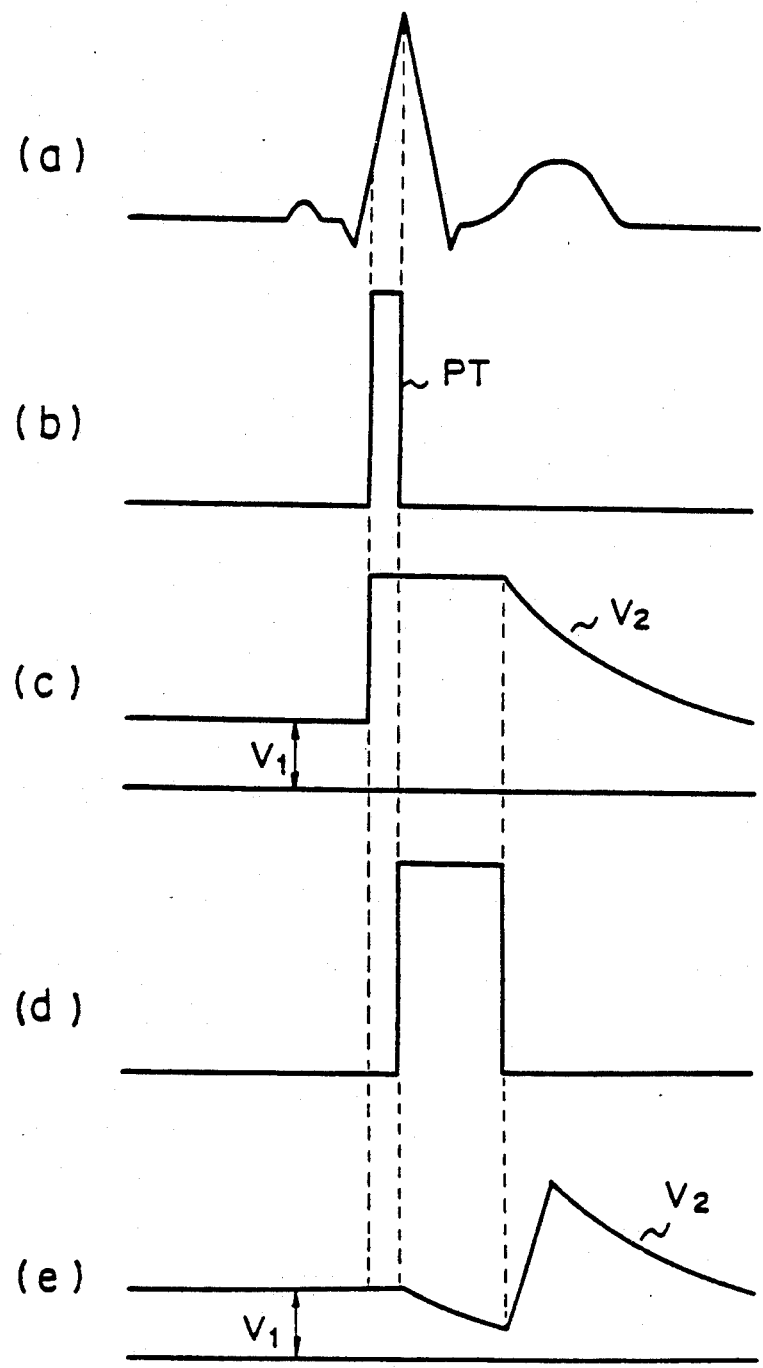
FIG. 5 shows the wave patterns of the respective portions in FIG. 1 and FIG. 4.
Figure 6:
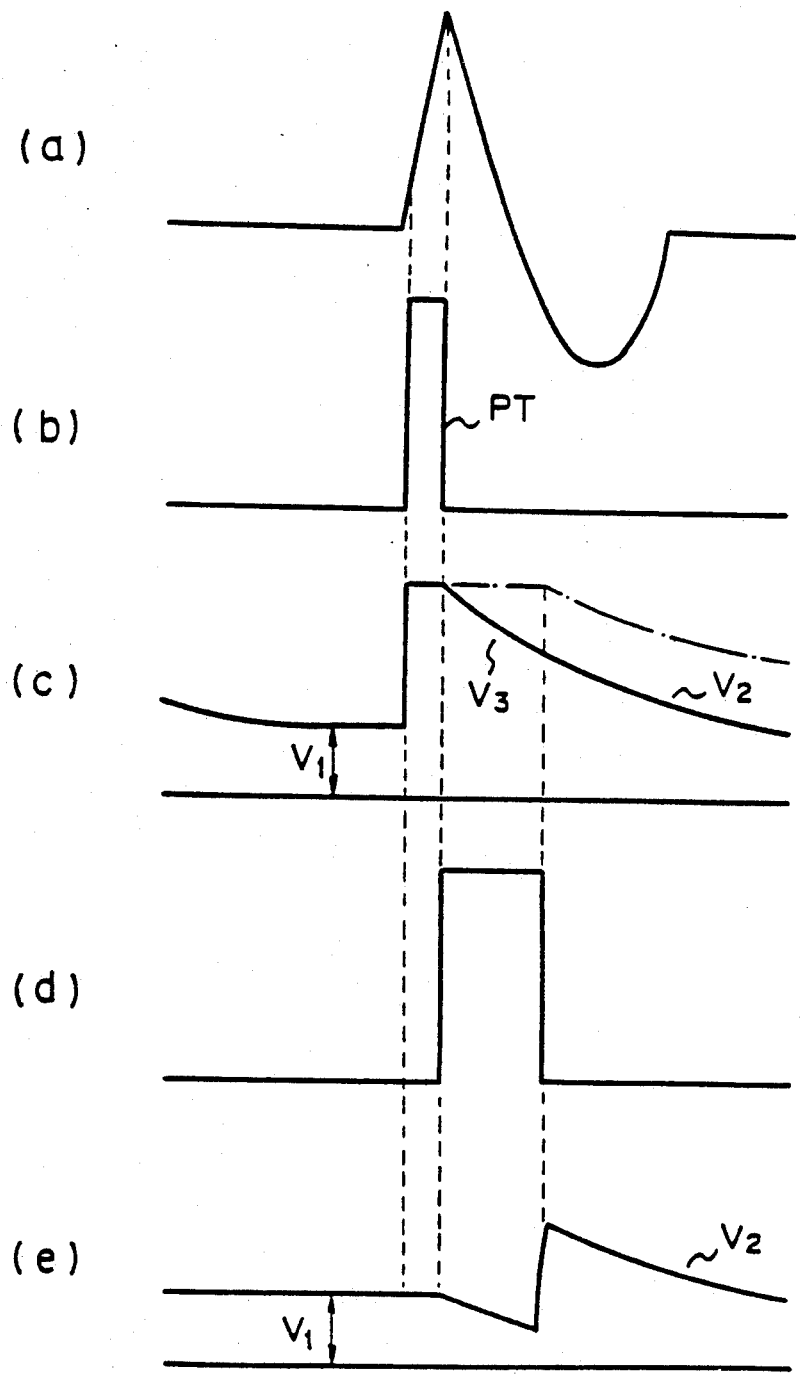
FIG. 6 shows the wave patterns of the respective portions in FIG. 1 and FIG. 4 when a deformed R-wave is input.

Next, referring to the wave patterns of the respective portions shown in FIG. 5 and FIG. 6, the action of the second embodiment of the device for detecting an R-wave in an electrocardiogram according to the present invention is to be described.

The input (1) in the comparator (41) corresponds to the wave pattern (a) in FIG. 5 and FIG. 6, the output (n) from the comparator (41) to the wave pattern (b) in FIG. 5 and FIG. 6, the input (m) in the comparator (41) to the wave pattern (c) in FIG. 5 and FIG. 6, the output from the delay circuit (49) to the wave pattern (d) in FIG. 5 and FIG. 6, and the voltage value at the second accumulation circuit to the wave pattern (e) in FIG. 5 and FIG. 6, respectively.

Initial state

The state from the initiation of actuation of the device for detecting an R-wave in an electrocardiogram according to the present invention to the arrival of the first R-wave is called the initial state. In this initial state, the input ends in the logical operation circuit (43) are both "0" level, the output is "1" level, and the switch (44) is closed. The input end (m) in the comparator exhibits the second reference voltage $V_1$ (V).

Input of R-Wave state

As shown in FIG. 5, with a rise of R-wave, the potential at the input end (l) in the comparator becomes higher than the potential of the voltage $V_1$ (V) applied to the input end (m), whereby the output from i; the comparator (41) becomes "1" level. The output from the output end (n) of the comparator (41) is input as R-wave pulses to the first accumulation circuit (42), the logical operation circuit (43) and the delay circuit (49), to the input end (o) of the limiting circuit (50). The output from the comparator (41) input to the first accumulation circuit (42) elevated the potential at the input end (m) of the comparator (41). The output (n) from the comparator (41) input to the logical operation circuit (43) makes the output from the logical operation circuit (43) "0" level, opening the switch (44), and the input (m) in the comparator (41) becomes in the state at 20 which the peak value in FIG. 5(c) is held.

After passing R-wave peak

After the R-wave peak has passed, the potentials at both input ends (l) and (m) in the comparator are reversed, and the output from the comparator (41) becomes "0" level. Accordingly, the fall of the output (n) from the comparator (41) is the time at the peak point of the R-wave (peak time phase), indicated by the PT portion in FIG. 5(b) and FIG. 6(b).

On the other hand, a delayed delay pulse is output from the delay circuit (49), and the switch (46) and the switch (48) are closed. Further, the delay pulse is also input to the input end (p) in the limiting circuit (50), and the output end B in FIG. 4 is compulsorily made "0" level at the time corresponding to the delay pulse width. When the switch (48) is closed, as shown in FIG. 5(e), the charges accumulated in the second accumulation circuit are discharged. When the switch (46) is closed, the voltages at the first accumulation circuit 42 and the second accumulation circuit (47) are compared within the adjusting circuit (45). Then, with the fall of the delay pulse in the delay circuit, the switches (48) and (46) are opened, while the switch (44) is closed, whereby the charges accumulated in the first accumulation circuit (42) are migrated to the second accumulation circuit (47) and the voltage drops as shown in FIG. 5(c) to approach the second reference voltage $V_1$ (V).

Deformed R-wave input

The abnormal electrocardiogram shown in the wave pattern in FIG. 6 has a very high peak amplitude of the R-wave or a broad QRS width, different from the normal electrocardiogram as shown in FIG. 3 or FIG. 5. This is a ventricular ectopic, a block wave pattern, etc., which sometimes appears in normal persons.

In such a case, the charges in the first accumulation circuit (42) become greater than usual, and therefore, after discharge by time constant, the potential at the input end (m) in the comparator becomes greater than the peak voltage of the subsequent R-wave, and thus, in some cases, an R-wave cannot be detected. Accordingly, while the delay pulse output from the delay circuit is at the "1" level, the voltage value at the first accumulation circuit (42) is compared with that of the second accumulation circuit (47). Here, since the voltage value at the first accumulation circuit does not surpass the voltage value at the second accumulation circuit, the voltage thereof becomes as shown by the wave pattern (c) in FIG. 6. The above action is carried out by the adjusting circuit (45), and the voltage value at the second accumulation circuit becomes a constantly stable voltage by the discharge effected when the delay pulse is "1" level.

As described above, this invention has the effects of holding the phase (time phase) of R-wave by a combination of a peak hold circuit and a reference voltage setting circuit, effectively discriminating the R-wave from noise in an electrocardiogram by providing a reference voltage set greater than the noise amplitude voltage, and also stably detecting an R-wave deformed by arrhythmia, and further, effectively prevents a T-wave being taken for an R-wave by providing a delay circuit thereby appropriately setting the delay time, as shown in the second example.

I claim:

1. A device for detecting an R-wave in an electrocardiogram comprising:

(a) a filter means for passing frequency components including an R-wave from an electrocardiogram input;

(b) a comparator for outputting an R-wave pulse when an input voltage passed through the filter means is higher than a reference voltage, said comparator having two input terminals, the first of said input terminals being coupled to the filter means so as to receive signals passed through the filter means;

(c) a first accumulation circuit connected to the comparator for accumulating charges output by the comparator and for outputting the reference voltage to the second input terminal of the comparator, the reference voltage being formed by accumulating the R-wave pulse from the comparator and by a predetermined voltage from a second accumulation circuit;

(d) a second accumulation circuit for accumulating the predetermined voltage, including means for connecting said second accumulation circuit to said first accumulation circuit when a digital pulse is output from a logical operation circuit means;

(e) a delay circuit connected to the comparator for converting the R-wave pulse to a delay pulse and for outputting the delay pulse having a predetermined pulse width after the output from the comparator has fallen;

(f) a logical operation circuit means connected to the comparator and the delay circuit for disconnecting the first accumulation circuit and the second accumulation circuit when the R-wave pulse from the comparator is output or when the delay pulse from the delay circuit is output and for connecting the first and second accumulation circuits at any other occasion; and (g) an adjusting circuit, including means for connection to the second accumulation circuit, connected to the first accumulation circuit for adjusting the voltages of the first and second accumulation circuit when the delay pulse is output from the delay circuit so that the voltage of the first accumulation circuit is lowered by electrically charging or discharging the first and second accumulation circuits.

2. A device for detecting an R-wave in an electrocardiogram as claimed in claim 1, further comprising a limiting circuit connected to the comparator for directly outputting the output of the comparator when the delay pulse is not output from the delay circuit, and not outputting the output from the comparator when the delay pulse is output from the delay circuit.

* * * * *

UNITED STATES PATENT AND TRADEMARK OFFICE
CERTIFICATE OF CORRECTION

PATENT NO. : 5,065,766
DATED : November 19, 1991
INVENTOR(S) : Minoru SASKI It is certified that error appears in the above-identified patent and that said Letters Patent is hereby corrected as shown below:

Claim 1, column 6, lines 35 and 36, change "circuit" to

--circuits--.

Signed and Sealed this

Twenty-fifth Day of May, 1993

Attest:

MICHAEL K. KIRK

*Attesting Officer*    Acting Commissioner of Patents and Trademarks